(12) United States Patent
Jacquet

(10) Patent No.: US 7,914,829 B2
(45) Date of Patent: Mar. 29, 2011

(54) ORAL COMPOSITION A FIRST COMPOSITION (A) AND A SECOND COMPOSITION (B) AS A COMBINATION PRODUCT FOR SEPARATE OR CONSECUTIVE ADMINISTRATION IN THE COSMETIC TREATMENT OF THE HUMAN BODY

(75) Inventor: Baudry Jacquet, Hasselt (BE)

(73) Assignee: Laboratoires Macanthy S.A., Monaco (MC)

( * ) Notice: Subject to any disclaimer, the term of this patent is extended or adjusted under 35 U.S.C. 154(b) by 204 days.

(21) Appl. No.: 10/578,089

(22) PCT Filed: Nov. 2, 2004

(86) PCT No.: PCT/IB2004/003884
§ 371 (c)(1),
(2), (4) Date: Jan. 3, 2007

(87) PCT Pub. No.: WO2005/041916
PCT Pub. Date: May 12, 2005

(65) Prior Publication Data
US 2007/0212407 A1     Sep. 13, 2007

(30) Foreign Application Priority Data
Nov. 3, 2003   (FR) .................... 03 12848

(51) Int. Cl.
*A61K 36/82*   (2006.01)
(52) U.S. Cl. ................................ 424/729

(58) Field of Classification Search .............. None
See application file for complete search history.

(56) References Cited

U.S. PATENT DOCUMENTS

| | | | | |
|---|---|---|---|---|
| 5,514,382 | A * | 5/1996 | Sultenfuss | 424/440 |
| 5,976,568 | A | 11/1999 | Riley | |
| 6,455,095 | B2 * | 9/2002 | Wong et al. | 426/634 |
| 6,471,969 | B1 | 10/2002 | Schlachter et al. | |
| 6,974,841 | B1 * | 12/2005 | Rapisarda | 514/783 |
| 2002/0098253 | A1 | 7/2002 | Riley | |
| 2003/0008048 | A1 | 1/2003 | Winston et al. | |
| 2004/0105894 | A1 * | 6/2004 | Gupta | 424/617 |
| 2005/0158396 | A1 | 7/2005 | Kraechter et al. | |

FOREIGN PATENT DOCUMENTS

| | | |
|---|---|---|
| EP | 0 075 633 B1 | 4/1983 |
| EP | 1 344 516 A1 | 9/2003 |
| FR | 2 809 596 | 12/2001 |
| WO | WO 02/15860 A | 2/2002 |
| WO | WO 02/100329 A2 | 12/2002 |
| WO | WO 03/086329 A2 | 10/2003 |

* cited by examiner

*Primary Examiner* — Christopher R. Tate
*Assistant Examiner* — Deborah A. Davis
(74) *Attorney, Agent, or Firm* — Young & Thompson

(57) ABSTRACT

The present invention relates to a composition suitable for oral delivery and including a first composition (a) containing a green tea extract and vitamin C, and optionally at least one metal compound selected from zinc, chromium and mixtures thereof, and a second composition (b) containing at least one metal compound selected from iron, copper, zinc, chromium and mixtures thereof, with the proviso that zinc and iron are not simultaneously present in the same composition, said composition being suitable for separate or consecutive use as a mixture in the cosmetic treatment of the human body.

19 Claims, No Drawings

ORAL COMPOSITION A FIRST COMPOSITION (A) AND A SECOND COMPOSITION (B) AS A COMBINATION PRODUCT FOR SEPARATE OR CONSECUTIVE ADMINISTRATION IN THE COSMETIC TREATMENT OF THE HUMAN BODY

This invention relates to a composition, intended for oral administration, comprising a first composition (a) and a second composition (b) as a combination product for separate or consecutive administration, in the cosmetic treatment of the human body. The first composition (a) contains a green tea extract, vitamin C, and optionally at least one metallic compound selected from zinc, chromium and a mixture thereof, and the second composition (b) contains at least one metallic compound selected from iron, copper, zinc, chromium and a mixture thereof, on the condition that zinc and iron are not simultaneously present in the same composition. The invention also relates to a method for cosmetic treatment of the human body involving the oral administration of a combination product comprising a first composition (a) and a second composition (b) for separate or consecutive administration.

Beauty, or at least physical appearance, is admittedly a significant preoccupation of contemporary society and, still today, more specifically women. This aesthetic preoccupation concerns the entire body, but more specifically the figure, the skin (in particular the skin of the face and hands), and the skin appendages (nails, hair).

To respond to this expectation, numerous products are made available to consumers, such as cosmetic products, drugs and, more recently, dietary supplements. Indeed, scientific studies have made it possible to establish that nutritional intake, in particular the intake of nutrients, vitamins and minerals, unsaturated fatty acids and some plant extracts, could have a large influence on physical appearance.

Today, there are many products (drugs and dietary supplements) intended for oral administration and designed to specifically enhance or correct the appearance of the skin, its appendages (hair and nails) and the figure. In practice, individuals concerned with their physical appearance must take at least three different products, each having a posology of two to three galenic forms (tablets, capsules, soft gel capsules, powder packets, drinkable solutions, etc.) each day. Therefore, there are six to nine galenic forms that these individuals may ingest each day in order to benefit from the desired effects. Aside from the fact that these administrations, due to their frequency, are very restrictive and easy to forget, the combination of products that have not been designed for simultaneous administration leads to risks of overdose or incompatibility between ingredients.

If one adds to this the fact that to preserve the physical appearance of youth or to enhance it, it is necessary to use these products continuously or at least over long periods, it is easy to understand the advantage of developing a product that is effective for all of these criteria, requiring the fewest number of administrations possible.

The applicant surprisingly discovered that the combination of green tea extract, vitamin C and metallic compounds selected from zinc, chromium, iron, and copper, in dietary supplements or food compositions, enabled a simultaneous action to be exerted on the following three targets: skin, skin appendages (hair, nails) and weight, by administering relatively low doses of products and a reduced number of daily administrations. In addition, the applicant discovered a way in which to administer these different products without any signs of incompatibility.

Moreover, green tea extract, vitamin C and metallic compounds selected from zinc, chromium, iron and copper according to this invention, are compounds that are cosmetically and nutraceutically acceptable, unaggressive, non-toxic, non-irritating for the skin, hypoallergenic, soothing, hydrating and anti-inflammatory for the skin. Additionally, these compounds are obtained by conventional extraction methods, and are available on the market.

This invention therefore relates to a composition, intended for oral administration, comprising:
- at least one first composition (a) containing a green tea extract and vitamin C, and optionally at least one metallic compound selected from zinc, chromium and a mixture thereof, and
- at least one second composition (b) containing at least one metallic compound selected from iron, copper, zinc, chromium and a mixture thereof, on the condition that the zinc and the iron are not simultaneously present in the same composition, wherein said metallic compounds of compositions (a) and (b) are advantageously in the form of salts or complexes, as a combination product for separate or consecutive administration, in the cosmetic treatment of the human body.

Advantageously according to this invention, the vitamin C on the one hand and the iron and copper on the other hand are not administered simultaneously in the same composition so as to avoid any risk of interference of their pro- and antioxidant activities. In addition, the zinc and the iron are not administered simultaneously in the same composition so as to avoid any risk of digestive absorption competition between these two elements.

In a specific embodiment of this invention, the green tea extract is an extract of green tea leaves, advantageously in powder form. This extract is conventionally obtained by green tea maceration in a solvent such as water, an alcohol-type solvent, hexane, or, advantageously, a water-alcohol mixture, then transformation into a powder by atomisation.

In another specific embodiment of this invention, the vitamin C is in the form of L-ascorbic acid, sodium L-ascorbate, calcium L-ascorbate, potassium L-ascorbate or L-ascorbyl 6-palmitate.

In another specific embodiment of this invention, the metallic compounds are in powder form. The zinc is advantageously in the form of zinc salt, such as zinc acetate, zinc chloride, zinc citrate, zinc gluconate, zinc lactate, zinc oxide, zinc carbonate or zinc sulphate. The zinc can also be in the form of a zinc-lysine, zinc-glycine or zinc-methionine complex.

The chromium is advantageously in the form of a chromium salt, such as chromium chloride (III) or chromium sulphate (III). The chromium can also be in the form of a chromium-lysine, chromium-glycine or chromium-methionine complex. The iron is advantageously in the form of an iron salt, such as ferrous carbonate, ferrous citrate, ammonium ferric citrate, ferrous gluconate, ferrous fumarate, sodium ferric diphosphate, ferrous lactate, ferrous sulphate, ferric pyrophosphate or diphosphate or ferric saccharate. The iron can also be in the form of basic iron (from carbonyl reduction, electrolytic reduction and hydrogen reduction), or an iron-lysine, iron-glycine or iron-methionine complex. The copper is advantageously in the form of a copper salt, such as copper carbonate, copper citrate, copper gluconate, or copper sulphate. The copper can also be in the form of a copper-lysine, copper-glycine or copper-methionine complex.

The term metallic complex in this invention refers to a metallic compound such as zinc, chromium, iron or copper combined with another compound such as amino acid, yeast or protein. Among the amino acids which can be used to form a metallic complex, lysine, glycine and methionine can be cited.

The composition according to this invention is advantageously intended to treat conditions and/or imbalances of the skin, skin appendages and/or overweight conditions. Thus, the composition can act on one of the following three targets: skin, skin appendages, weight, or on all three of these targets simultaneously.

The composition according to this invention can advantageously act to improve the appearance of the skin, in particular skin hydration, to improve skin density (reduce the appearance of "wilted" skin), the elasticity and firmness of the skin, as well as to reduce the depth of wrinkles. The composition according to this invention can also act to reduce the orange peel-like appearance of the skin (cellulite). The composition according to the invention can also advantageously act on the hair, in particular to reduce hair loss, improve hair strength, volume and brightness, as well as on the nails, in particular to improve their hardness and reduce the frequency of nail breakage. Finally, the composition according to this invention can also act to improve the figure and overweight conditions, in particular to reduce weight, and the volume of fat accumulation areas, in particular on the thighs and hips.

Advantageously according to this invention, composition (a) contains at least one green tea extract, vitamin C, a zinc salt and a chromium salt, and composition (b) contains at least one iron salt and one copper salt.

According to a specific feature of this invention, the concentration of green tea extract is between 1 and 50% by weight, advantageously between 2 and 50% by weight, even more advantageously between 5 and 30% by weight, and still more advantageously between 10 and 30% by weight, with respect to the total weight of composition (a).

According to another specific feature of this invention, the vitamin C is present at a concentration of between 0.5 and 50% by weight, advantageously between 2 and 50% by weight, even more advantageously between 2 and 30% by weight, and still more advantageously between 2 and 15% by weight, with respect to the total weight of composition (a).

According to another specific feature of this invention, the zinc is present at a concentration of between 0 and 3% by weight, advantageously between 0.2 and 3% by weight, even more advantageously between 0.2 and 1% by weight, and still more advantageously between 0.2 and 0.5% by weight, with respect to the total weight of composition (a) or composition (b) and/or the chromium is present at a concentration of between 0 and 1% by weight, advantageously between 0 and 0.05% by weight, even more advantageously between 0.0002 and 0.04% by weight, and still more advantageously between 0.001 and 0.04% by weight, with respect to the total weight of composition (a) or composition (b).

According to another specific feature of this invention, the iron is present at a concentration of between 0 and 10% by weight, advantageously between 0.2 and 10% by weight, and even more advantageously between 0.2 and 3% by weight, with respect to the total weight of composition (b), and/or the copper is present at a concentration of between 0 and 1% by weight, advantageously between 0.02 and 1% by weight, even more advantageously between 0.02 and 0.5% by weight, and still more advantageously between 0.02 and 0.2% by weight, with respect to the total weight of composition (b).

The composition according to this invention is advantageously a nutraceutical composition or a dietary supplement. In a specific embodiment of this invention, compositions (a) and (b) are in the form of capsules, gel caps, tablets, pellets, powders or drinkable solutions. When compositions (a) and (b) are in the form of soft gel capsules or gel caps, the shell of these soft capsules or gel caps can contain in particular animal gelatine such as fish gelatine or glycerine, or a plant-type material such as a cellulose or starch derivative, or plant protein. When the compositions are in the form of gel caps, tablets or pellets, the mixture of active ingredients can be set on a powdery medium such as silica, cellulose or maltodextrin.

Advantageously according to this invention, compositions (a) and (b) are both in the form of soft gel capsules or gel caps and the green tea extract is present at a concentration of between 10 and 30% by weight, with respect to the total weight of composition (a), the vitamin C is present at a concentration of between 2 and 15% by weight, with respect to the total weight of composition (a), the zinc is present at a concentration of between 0.2 and 0.5% by weight, with respect to the total weight of composition (a), the chromium is present at a concentration of between 0.001 and 0.04% by weight, with respect to the total weight of composition (a), the iron is present at a concentration of between 0.2 and 10% by weight, with respect to the total weight of composition (b), and the copper is present at a concentration of between 0.02 and 0.2% by weight, with respect to the total weight of composition (b). When compositions (a) and (b) are both in the form of soft gel capsules or gel caps, the phrase "by total weight of the composition" in this invention refers to the weight of the contents of the capsules or gel caps added to the weight of the shell of said capsules or gel caps.

Advantageously according to this invention, the composition is titrated so as to make it possible to administer a daily dose of 100 to 3000 mg, preferably 200 to 2000 mg, and more preferably 300 to 1500 mg, of green tea extract; from 50 to 1000 mg, and preferably 100 to 500 mg, of vitamin C; from 0 to 50 mg, preferably 1 to 50 mg, and more preferably 5 to 20 mg, of zinc; from 0 to 300 µg, preferably 10 to 300 µg, and more preferably 20 to 100 µg, of chromium; from 0 to 100 mg, preferably 1 to 100 mg, and more preferably 5 to 50 mg, of iron; and from 0 to 20 mg, preferably 0.5 to 20 mg, and more preferably 1 to 10 mg, of copper.

Advantageously according to this invention, the composition is a nutraceutical or dietary composition or supplement, and can include any suitable carrier or excipient that is acceptable from a cosmetic or nutraceutical perspective, as well as conventional additives, known to a person skilled in the art.

Advantageously according to this invention, the composition contains other active ingredients that can complement or reinforce the action of the main ingredients, namely vitamins such as provitamin A, carotenoids, B-group vitamins, in particular vitamins B2, B5, B6 and B8; other metallic salts such as selenium or manganese salts; unsaturated fatty acids such as borage oil or fish oil; grape-cake extract; or shark cartilage.

This invention also relates to a method for cosmetic treatment of the human body, characterised in that it involves the oral administration of a combination product comprising:
  at least one first composition (a) containing a green tea extract and vitamin C, and optionally at least one metallic compound selected from zinc, chromium and a mixture thereof, and
  at least one second composition (b) containing at least one metallic compound selected from iron, copper, zinc, chromium and a mixture thereof, on the condition that the zinc and the iron are not simultaneously present in the same composition,
wherein said metallic compounds of compositions (a) and (b) are advantageously in the form of salts or complexes, for separate or consecutive administration.

The method according to the invention is advantageously intended to treat conditions and/or imbalances of the skin, its appendages and/or to treat overweight conditions. Thus, the composition according to the invention (combination product) can act on one of the following three targets: skin, skin appendages, weight, or on all three of these targets simultaneously.

Advantageously according to this invention, composition (a) contains at least one green tea extract, vitamin C, a zinc salt and a chromium salt, and composition (b) contains at least one iron salt and one copper salt.

In a specific embodiment of the method of this invention, the various compounds of compositions (a) and (b) have the same concentrations as mentioned above.

According to a specific feature of this invention, the method involves the administration of a daily dose of green tea extract of between 100 and 3000 mg, advantageously between 200 and 2000 mg, and more advantageously between 300 and 1500 mg.

According to another specific feature of this invention, the method involves the administration of a daily dose of vitamin C between 50 and 1000 mg, advantageously between 60 and 500 mg, and more advantageously between 100 and 500 mg.

According to another specific feature of this invention, the method involves the administration of a daily dose of zinc between 0 and 50 mg, advantageously between 1 and 50 mg, and more advantageously between 5 and 20 mg, and/or a daily dose of chromium between 0 and 300 µg, advantageously between 10 and 300 µg, more advantageously between 12 and 100 µg, and still more advantageously between 20 and 100 µg.

According to another specific feature of this invention, the method involves the administration of a daily dose of iron between 0 and 100 mg, advantageously between 1 and 100 mg, more advantageously between 5 and 50 mg, and still more advantageously between 10 and 50 mg, and/or a daily dose of copper between 0 and 20 mg, advantageously between 0.5 and 20 mg, and more advantageously between 1 and 10 mg.

Advantageously according to this invention, composition (a) is administered in the first part of the day, in particular in the morning or at noon, and composition (b) is administered in the latter part of the day, in particular during the afternoon or the evening. The stimulating active ingredients of composition (a), namely the green tea and vitamin C, are thus advantageously administered in the first part of the day so as to avoid sleeping problems in the evening.

In a specific embodiment of this invention, compositions (a) and (b) are both in the form of soft gel capsules. Advantageously according to this invention, the administration of two capsules of composition (a) in the morning and one capsule of composition (b) in the evening make it possible to provide an effective dose of each of the necessary ingredients for acting on all three of the targets: skin, skin appendages and weight, while separating the incompatible active ingredients from one another.

The following examples are intended to illustrate the invention without limiting its scope in any way. Unless otherwise specified, the percentages indicated in the following examples are percentages by weight.

EXAMPLES OF COMPOSITIONS ACCORDING TO THIS INVENTION AND THE METHODS FOR PREPARATION THEREOF

Example 1

Compositions (a) and (b) Are in the Form of Soft Gel Capsules—Preparation Method Composition (a):

| Ingredients | Amounts per capsule |
| --- | --- |
| Borage oil | 357 mg |
| Green tea extract | 200 mg |
| Calcium ascorbate (vitamin C) | 75 mg |
| Natural beta carotene (vitamin A) | 2.4 mg |
| Lecithin | 13.6 mg |
| Yellow beeswax | 10.8 mg |
| Chromium chloride | 0.06 mg |
| Zinc sulphate | 13.7 mg |
| Sodium selenate | 0.05 mg |
| Capsule shell | Fish gelatine, glycerine, water and food colouring |

Composition (b):

| Ingredients | Amounts per capsule |
| --- | --- |
| Concentrated fish oil | 365 mg |
| Grape-cake extract | 150 mg |
| Shark cartilage | 100 mg |
| Iron fumarate | 31.8 mg |
| Copper sulphate | 2.6 mg |
| Yellow beeswax | 15 mg |
| Vitamin B2 (Riboflavin) | 1.6 mg |
| Vitamin B5 (calcium pantothenate) | 6.55 mg |
| Vitamin B6 (pyridoxine chlorhydrate) | 2.4 mg |
| Vitamin B8 (biotin) | 0.15 mg |
| Lecithin | 12 mg |
| Capsule shell | Fish gelatine, glycerine, water and food colouring |

Method for Preparing Compositions (a) and (b):

The method consists of dispersing by agitating the lecithin and the beeswax in the heated majority oil (borage for composition (a) and fish oil for composition (b)), then incorporating, still while agitating, the various ingredients in the aforementioned mixture.

This mixture is then encapsulated in a shell consisting of gelatine, glycerine, water and colouring by means of a specific machine for this type of operation (soft gel capsule production machine), then the soft gel capsules are dried (removal of some of the water from the shell).

Example 2

Evaluation of the Activity Induced by the Administration of Compositions According to this Invention on the Four Targets: Skin, Hair, Nails and Weight Compositions (a) and (b) of example 1 were administered to volunteers in an amount of 2 capsules of composition (a) in the morning and 1 capsule of composition (b) in the evening for 2 months. The volunteers, of female sex and over 40 years of age, were selected because they satisfied at least one of the following criteria:

regular hair loss for more than one week (method for collecting hair loss by the volunteer), facial wrinkles (crow's feet) having a depth of at least 0.3 mm by profilometric measurement (silicone imprint), objective skin dryness on the legs, determined by a questionnaire completed by the volunteers, breaking nails requiring very regular cutting, overweight condition defined by a BMI (Body Mass Index) over 25.

The results observed were as follows after 2 months of treatment:

hair loss, reduced by 32%,

40% reduction in depth of wrinkles, improvement of skin dryness in 73% of the volunteers, improvement of nail solidity in 64% of the volunteers, average weight loss of 5.1 kg.

Example 3

Clinical Evaluation of the Activity Induced by the Administration of Compositions According to this Invention on the Four Targets: Skin, Hair, Nails and Weight The following compositions were administered to women in an amount of 2 capsules in the morning and 1 capsule in the evening. The abbreviation "RDA" stands for "Recommended Daily Allowances".

Capsules for the Morning:

| Ingredients | For 2 capsules | % RDA |
|---|---|---|
| Green tea aqueous extract | 400 mg | |
| Vitamin C | 120 mg | 200% |
| Natural beta carotene | 800 µg ER | 100% |
| Zinc | 10 mg | 67% |
| Selenium | 40 µg | 80% |
| Chromium | 25 µg | 100% |
| Borage oil | 700 mg | |

Capsule for the Evening:

| Ingredients | For 1 capsule | % RDA |
|---|---|---|
| Grape extract | 150 mg | |
| Shark cartilage | 100 mg | |
| Vitamin B2 | 1.6 mg | 100% |
| Vitamin B5 | 6 mg | 100% |
| Vitamin B6 | 2 mg | 100% |
| Vitamin B8 | 150 µg | 100% |
| Copper | 1 mg | 50% |
| Iron | 10 mg | 71% |
| Fish oil | 350 mg | |

Hair Loss Study

This study was conducted on 30 women over 30 years of age (average age 48.8 years; min: 35 years, max: 67 years) having abnormal hair loss for several months. The evaluation of the efficacy was based on an experimentally-validated technique of collecting hair lost during brushing.

Each woman had to perform a standardised brushing of her dry hair once per day, collect the hair that had fallen and been collected by the brush, and insert it into a pre-weighed plastic bottle. This daily hair collection was performed during the month preceding the beginning of the treatment, and during the entire second month of treatment with the aforementioned compositions according to the invention.

The results demonstrate a real activity of the compositions according to the invention on hair loss, since the average daily hair loss was initially 52 mg per day, and was only 21.6 mg per day during the second month of the capsule administration, that is a very significant reduction of more than 50%.

This highly objective evaluation obtained by the weighing of hair by the research team was confirmed by the volunteers: 85% of women observed a clear reduction in their hair loss.

Weight Loss Study

This study was conducted on 22 women over 30 years of age (average age: 48.3 years) having an overweight condition defined by a ratio: weight (kg)/height (cm)$^2$ between 25 and 30 (average 27.8).

The study was conducted over 2 months, with each volunteer taking a daily dose of 2 capsules in the morning and 1 capsule in the evening, as described above. The protocol required the volunteers to change nothing in their dietary habits during the period of the study and, in particular, not to begin or continue a low-calorie weight-loss diet.

Each volunteer was seen 3 times by the physician: before the beginning of the study, after 1 month of administration, and after 2 months of administration. The criteria evaluated were weight, fat content, measured by a metric impedance scale, and the perimeters of the thighs and the abdomen, measured by a reproducible technique ensuring that the measurements for each patient at each visit were performed at exactly the same level.

The results were as follows:

weight: a statistically significant weight loss was observed starting in the first month, and reached 1.2 kg after 2 months of administration, fat content: a statistically significant reduction in fat content was observed starting in the first month, and reached 0.882 kg after 2 months of administration, perimeter of thighs: very significant reduction starting in the first month (0.9 cm) which continued through the second month, to reach 1.3 cm, and perimeter of the abdomen: a statistically significant reduction was observed beginning in the first month (1 cm) and continued significantly through the second month (1.9 cm).

Wrinkle Study

Among the 52 women who participated in one of the two studies ("weight loss" or "hair"), 17 had, at the time of inclusion, at least one notable wrinkle in the area of the crow's feet. For these 17 women, a silicon imprint was taken before and at the end of the study.

The study lasted 2 months. The women took the capsules daily for the entire duration of the study.

These prints were then analysed by laser profilometry enabling the exact sizes (length, width and depth) of the wrinkle to be measured to the nearest micrometer. This profilometric analysis of the print made it possible to calculate a number of parameters:

complexity: this is the ratio between the developed skin surface and the horizontal projection of this surface;

depth: average depth of the wrinkle in the surface analysed;

volume: average volume of the wrinkle in the surface analysed.

The results obtained were highly advantageous:

the average complexity went from 24.5% to 17.6%, i.e. a reduction of 25%;

the average depth went from 320 µm to 213 µm, i.e. a reduction of 27%;

the average volume went from 0.595 mm³ to 0.400 mm³, i.e. a reduction of 23%.

The study thus made it possible to show that the administration of compositions according to the invention enabled wrinkles to be significantly reduced in terms of visibility.

Skin Hydration Study

The measurement of skin hydration on the external surface of the legs was performed using a corneometer before and after the study, on all 52 women.

The average level of skin hydration was 54.47 before the study, 56.73 after 1 month, and 61.71 after 2 months. This improvement in skin hydration was therefore very statistically significant starting in the first month of use.

Nail Study

Out of the 52 women who participated in one of the two weight loss or hair studies, 26 women complained, at the time of recruitment, of nail problems. The 2 problems most commonly encountered were splitting nails and breaking nails.

After 2 months of taking the capsules according to the invention, 70% of the women noted a clear, and often spectacular, improvement in the quality of their nails.

To conclude, the compositions according to the invention make it possible to cause weight loss and to improve the figure, reduce hair loss, reduce wrinkles, improve skin hydration, and/or improve the quality of nails, in particular breaking nails.

The invention claimed is:

1. A method for treating conditions of hair said treating selected from the group consisting of reducing hair loss and improving hair strength, hair volume and hair brightness of a human in need thereof, comprising orally administering to said human an effective amount of a combination product comprising:
   a first composition (a) containing a green tea extract, vitamin C, zinc and optionally chromium, and
   a second composition (b) containing at least iron and copper,
   said compositions (a) and (b) being separately and consecutively orally administered to said human, wherein zinc and iron are not simultaneously present in the same composition.

2. The method according to claim 1, wherein composition (a) contains at least one green tea extract, vitamin C, a zinc salt and a chromium salt, and composition (b) contains at least one iron salt and one copper salt.

3. The method according to claim 1, wherein the combination product is orally administered as a daily dose thereof, and wherein the green tea extract in the daily dose is between 100 and 3000 mg.

4. The method according to claim 1, wherein the combination product is orally administered as a daily dose thereof, and wherein the daily dose of vitamin C in the daily dose is between 50 and 1000 mg.

5. The method according to claim 1, wherein the combination product is orally administered as a daily dose thereof, and wherein the daily dose of zinc in the daily dose is between 1 and 50 mg and the daily dose of chromium in the daily dose is between 0 and 300 ug.

6. The method according to claim 1, wherein the combination product is orally administered as a daily dose thereof, and wherein the daily dose of iron in the daily dose is between 1 and 100 mg, and the daily dose of copper in the daily dose is between 0.5 and 20 mg.

7. The method according to claim 1, wherein composition (a) is administered in the first part of the day and composition (b) is administered in the second part of the day.

8. The method according to claim 1, wherein the combination product is orally administered as a daily dose thereof, and wherein a daily dose of green tea extract in the daily dose is between 200 and 2000 mg.

9. The method according to claim 1, wherein the combination product is orally administered as a daily dose thereof, and wherein the daily dose of vitamin C in the daily dose is between 100 and 500 mg.

10. The method according to claim 1, wherein the combination product is orally administered as a daily dose thereof, and wherein the daily dose of zinc in the daily dose is between 5 and 20 mg, and the daily dose of chromium in the daily dose is between 20 and 100 ug.

11. The method according to claim 1, wherein the combination product is orally administered as a daily dose thereof, and wherein the daily dose of iron in the daily dose is between 5 and 50 mg, and the daily dose of copper in the daily dosage is between 1 and 10 mg.

12. The method according to claim 1, wherein the green tea extract is present at a concentration of between 2 and 50% by weight with respect to the total weight of composition (a).

13. The method according to claim 1, wherein the vitamin C is present at a concentration of between 0.5 and 50% by weight, with respect to the total weight of composition (a).

14. The method according to claim 1, wherein the zinc is present at a concentration of between 0.2 and 3% by weight, with respect to the total weight of composition (a) and the chromium is present at a concentration of between 0 and 1% by weight, with respect to the total weight of composition (a).

15. The method according to claim 1, wherein the iron is present at a concentration of between 0.2 and 10% by weight, with respect to the total weight of composition (b) and the copper is present at a concentration of between 0.02 and 1% by weight, with respect to the total weight of composition (b).

16. The method according to claim 1, wherein compositions (a) and (b) are in the form of capsules, gel caps, tablets, pellets, powders or drinkable solutions.

17. The method according to claim 1, wherein,
   the first composition (a) further comprises selenium to compliment or reinforce the green tea extract, the vitamin C, the zinc and the optional chromium, and
   the second composition (b) further comprises grape seeds extract, shark cartilage extract, and B-group vitamins to compliment or reinforce the iron and the copper.

18. A method for treating skin conditions, said treating selected from the group consisting of improving skin hydration and reducing wrinkle depth of a human in need thereof, comprising orally administering to said human an effective amount of a combination product comprising:
   a first composition (a) containing a green tea extract, vitamin C, zinc and optionally chromium, and
   a second composition (b) containing at least iron and copper, said compositions (a) and (b) being separately and consecutively orally administered to said human, wherein zinc and iron are not simultaneously present in the same composition.

19. A method for treating nail conditions, said treating selected from the group consisting of improving nail hardness and reducing nail breakage frequency of a human in need thereof, comprising orally administering to said human an effective amount of a combination product comprising:

a first composition (a) containing a green tea extract, vitamin C, zinc and optionally chromium, and a second composition (b) containing at least iron and copper, said compositions (a) and (b) being separately and consecutively orally administered to said human, wherein zinc and iron are not simultaneously present in the same composition.

* * * * *